United States Patent [19]

Calabresi et al.

[11] Patent Number: 5,478,804
[45] Date of Patent: Dec. 26, 1995

[54] TREATMENT OF TUMORIGENIC PATHOPHYSIOLOGICAL CONDITIONS WITH FGF-CYTOXIC CONJUGATES

[75] Inventors: Paul Calabresi, Barrington; Julie G. Beitz, Rumford; Jeffrey W. Clark, Providence; A. Raymond Frackelton, Jr., Rumford, all of R.I.; Douglas A. Lappi, Del Mar; Andrew J. Baird, San Diego, both of Calif.

[73] Assignees: The Salk Institute for Biological Studies, San Diego, Calif.; Roger Williams General Hospital, Providence, R.I.

[21] Appl. No.: 250,097

[22] Filed: May 26, 1994

Related U.S. Application Data

[63] Continuation of Ser. No. 30,218, Mar. 23, 1993, abandoned, which is a continuation-in-part of Ser. No. 585,319, filed as PCT/US91/06680, Sep. 13, 1991, abandoned.

[51] Int. Cl.$^6$ ............................ A61K 38/18; A61K 38/43
[52] U.S. Cl. .................................. 514/2; 514/8; 424/94.1
[58] Field of Search ........................... 514/2, 8; 530/399, 530/370, 402; 424/94.1

[56] References Cited

U.S. PATENT DOCUMENTS

| | | | |
|---|---|---|---|
| 4,468,382 | 8/1984 | Bacha et al. | 424/177 |
| 5,084,556 | 1/1992 | Brown | 530/351 |
| 5,087,616 | 2/1992 | Myers et al. | 514/21 |
| 5,116,753 | 5/1992 | Beattie et al. | 435/240.2 |
| 5,169,933 | 12/1992 | Anderson et al. | 424/85.91 |
| 5,191,067 | 3/1993 | Lappi et al. | 530/399 |
| 5,308,622 | 5/1994 | Casscells et al. | 514/21 |

FOREIGN PATENT DOCUMENTS

| | | |
|---|---|---|
| 0259904 | 3/1988 | European Pat. Off. . |
| 0305967 | 3/1989 | European Pat. Off. . |
| 8503508 | 8/1965 | WIPO . |
| 9002800 | 3/1990 | WIPO . |

OTHER PUBLICATIONS

Halaban et al, "BFGF is the Putative Natural Growth Factor for Human Melanocytes", *In Vitro Cell & Devel. Biol.* 23(1): 47–52. (Jan. 1987).

Imamura et al., "Purification of basic FGF receptors from rat brain," *B.B.R.C.*, 155(2):583–590 (1988).

Huang and Huang, "Association of bovine brain–derived growth factor receptor with protein tyrosine kinase activity", *J. Biol. Chem.*, 261:9568–9571 (1986).

Neufeld et al., "The identification and partial characterization of the fibroblast growth factor receptor of baby hamster kidney cells," *J. Biol. Chem.*, 260:13860–13860 (1985).

Neufeld et al., "Basic and Acidic fibroblast growth factors interact with the same cell surface receptors," *J. Biol. Chem.*, 261:5631–5637 (1986).

Blakey et al., "Comparison of the pharmacokinetics and hepototoxic effects of saporin and ricin A–chain immunotoxins on murine liver parenchymal cells," *Cancer Research*, 48:7072–7078 (1988).

Halaban et al., "bFGF as an autocrine growth factor for human melanomas," *Oncogene Research*, 3:177–186 (1988).

(List continued on next page.)

*Primary Examiner*—Stephen G. Walsh
*Attorney, Agent, or Firm*—Fitch, Even, Tabin & Flannery

[57] ABSTRACT

Conjugates comprising bFGF or other FGF polypeptides and a cytotoxic agent are prepared. The cytotoxic agent can be a ribosome-inactivating protein (RIP), such as saporin, which is attached to bFGF through a chemical bond, or the composition can be prepared as a recombinant DNA chimera. The conjugates are used to specifically target cells, in vivo and in vitro, which express FGF receptors. The cytotoxicity of the conjugates is proportional to the number of receptors expressed by a cell type. The conjugate is useful to effectively treat mammals, and in particular human patients, afflicted with tumorigenic conditions, such as human melanomas, human ovarian carcinomas, teratocarcinomas and neuroblastomas, and other FGF-mediated tumors caused by a proliferation of cells which express FGF receptors.

19 Claims, 5 Drawing Sheets

OTHER PUBLICATIONS

Baird et al., "Fibroblast growth factors" *British Med. Bull.*, 45(2):438–452 (1989).

Barbieri et al., "Ribosome-inactivating proteins from plants: Properties and possible uses," *Cancel Surveys*, 1(3):489–520 (1982).

Beattie et al., "Selective elimination of fibroblasts from pancreatic islet monolayers by basic fibroblast growth factor–saporin mitotoxin," *Diabetes*, 39(8):1002–1005 (1990).

Bergamaschi et al., "Killing of K562 cells with conjugates between human transferrin and a ribosome-inactivating protein (SO–6)," *British J. Haematology*, 68:379–384 (1988).

Grindey, G., "Current status of cancer drug development: Failure or limited success?" *Cancer Cells*, 2(6):163–171 (1990).

Lappi et al., "Mitotoxins: Growth factor-targeted cytotxic molecules," *Progress in Growth Factor Research*, 2:223–226 (1990).

Lappi et al., "Characterization of a *Saponaria officinalis* seed ribonsome-inactivating protein: Immunoreactivity and sequence homologies," Biochem. Biophys. Res.Comm., 129)3):934–942 (1985).

Lappi et al., "Biological and chemical characterization of basic FGF–saporin mitotoxin," *Biochem. Biophys. Res. Comm.*, 160(2):917–923 (1989).

Lappi et al., "Basic fibroblast growth factor–saporin mitotoxin: An endothelial cell growth inhibitor," *J. Cell. Biochem.*, Supp. 14E, UCLA Symposium on Molec. & Cell. Biol. Abstracts, 19th Annual Mtg., 31 Mar. to 22 Apr. 1990, N.Y., p. 222 (1990).

Montecucci et al., "N–terminal sequence of some ribosome-inactivating proteins," *Int. J. Peptide Protein Res.*, 33:263–267 (1989).

Olwin et al., "Cell type and tissue distribution of the fibroblast growth factor receptor," *J. Cell. Biochem.*, 39:443–454 (1989).

Soria, M., "Immunotoxins, ligand–toxin conjugates and molecular targeting," *Pharm. Res.*, 21(2):35–46 (1989).

Stripe et al., "Ribosome-inactivating proteins from the seeds of *Saponari a officinalis L.* (soapwart), of *Agrostemma githago L.* (corn cockle) and of *Asparagus officinalis L.* (asparagus), and from the latex of *Hura crepitans L.* (sandbox tree)," *Biochem. J.*, 216:617–625 (1983).

Whalen et al., "The fate of intravenously administered bFGF and the effect of heparin," *Growth Factors*, 1:157–164 (1989).

Woodbury et al., "Identification of a cell surface protein, p. 97, in human melanomas and certain other neoplasms," *Proc. Natl. Acad. Sci.*, 787(4):2183–2187 (1980).

Folkman et al., "Heparin affinity: Purification of a tumor–derived capillary endothelial cell growth factor," *Science* 223:1296–1299(1984).

Moscatelli, D., "High and low affinity binding sites for basic fibroblast growth factor on cultured cells:Absence of a role for low affinity binding in the stimulation of plasminogen activator production by bovine capillary endothelial cells," *J. Cell. Physio.* 131:123–130 (1987).

TREATMENT OF TUMORIGENIC PATHOPHYSIOLOGICAL CONDITIONS WITH FGF-CYTOXIC CONJUGATES

This invention was made with Government support under Grant No. DK-18811 and Grant CA-13943-19 awarded by the National Institutes of Health. The Government has certain rights in this invention. This is a continuation of application filed Mar. 23, 1993, now abandoned, which was the natural stage of PCT/U.S. 90/06680, Ser. No. 08/030,218 filed on Sep. 13, 1991 which is a Continuation-in-Part of U.S. application Ser. No. 07/585,319, filed Sep. 19, 1993, which has been abandoned.

This invention relates to the use of particular conjugates which are targeted to inhibit cell proliferation, and more specifically, to the use of fibroblast growth factor conjugated to a cytotoxic agent.

BACKGROUND OF THE INVENTION

Angiogenesis plays a critical role in embryonic development and in several physiologic and pathologic conditions, including wound healing, ovulation, diabetic retinopathy and malignancy. In particular, without the nutrients and oxygen provided via this neovascularization, solid tumors would be unable to grow beyond about 2 mm in diameter.

New capillary growth takes place by a series of sequential steps beginning with the dissolution of the capillary basement membrane. Microvascular endothelial cells stimulate a by angiogenic substances, such as basic fibroblast growth factor (bFGF), in vitro secrete collagenase, plasminogen activator, and stromelysin which degrade the basement membrane and allow endothelial cells to migrate toward the angiogenic stimulus. After migrating, the endothelial cells proliferate, develop sprouts, form capillary-like hollow tubules, and finally link tubules into capillary loops.

Basic FGF is a protein which has a molecular weight of approximately 16 kD, is acid- and temperature-sensitive and has a high isoelectric point. A structurally related protein, acidic FGF (aFGF), has an acidic isoelectric point. FGFs exhibit a mitogenic effect on a wide variety of mesenchymal, endocrine and neural cells. Of particular interest is their stimulatory effect on collateral vascularization and angiogenesis. Such mitogenic effects have stimulated considerable interest in FGFs as potential therapeutic agents for wound healing, nerve regeneration and cartilage repair for example.

Many cells that respond to FGF have been shown to possess specific receptors on the cell surface membranes. The receptor proteins appear to be single chain polypeptides with molecular weights ranging from 110 to 165 kD, depending on cell type. The proteins bind basic FGF with high affinity (Kd=10–80 pM), with receptor numbers ranging from 2000 to 80,000 per cell. Such receptors have been purified from rat brain, using a combination of lectin and ligand affinity chromatography and are associated with tyrosine kinase activity, see Imamura et al., *B.B.R.C.* 155, 583–590 (1989); Huang and Huang, *J. Biol. Chem.*, 261, 9568–9571 (1986).

On baby hamster kidney cells (BHK), two basic FGF receptors with estimated molecular weights of 110 and 130 kD have been reported in Neufeld et al., *J. Biol. Chem.*, 260, 13860–13868 (1985) and Neufeld et al., *J. Biol. Chem.*, 261, 5631–5637 (1986). Both receptor proteins bind basic FGF and acidic FGF, although it appears that the larger receptor protein binds bFGF preferentially and is sometimes referred to as the "high affinity" bFGF receptor; the smaller receptor has somewhat greater affinity for acidic FGF. Other studies have uncovered additional common FGF receptors in cultured cell lines and embryonic tissues which will bind both bFGF and aFGF, see Olwin et al. *J. of Cell. Biochem*, 39, 443–454 (1989).

The feasibility of using receptor-specific ligands to transport toxins into cells has recently been demonstrated. The strategy, originally applied in immunotherapy by conjugating toxins to monoclonal antibodies (see Blakey et al., *Cancer Research*, 48, 7072–7078 (1988)), has recently been pursued by coupling toxins with classic endocrine hormones, such as CRF and TRF, with cytokines such as EGF and TGFα and with lymphokines such as interleukin-2. U.S. Pat. No. 4,468,382 to Bacha et al. shows cytotoxic conjugates having a disulfide bond with a histidine residue to produce a toxic hybrid protein alleged to be useful in the treatment of certain tumors.

Fibroblast growth factor (FGF) has been coupled with cytotoxins to produce FGF conjugates which are mitotoxic. As detailed in Lappi, et al. *B.B.R.C.* 160, 917–923 (1989), basic FGF has been coupled to saporin-6 (SAP), a ribosome-inactivating protein (RIP) isolated from the seeds of the plant *Saponaria officinalis* to produce FGF-SAP, which is shown to be a powerful mitotoxin.

Human melanoma is an example of a cancer that has been steadily rising in incidence and is highly refractory to conventional modes of therapy. In Halaban et al., *Oncogene Research*, 3, 177–186(1988), it was reported that melanoma cells express bFGF transcripts and suggested the bFGF may act as an autocrine growth factor therefor.

A present need exists for developing improved methods of treating melanomas and other cancerous tumors which currently have a low cure rate.

SUMMARY OF THE INVENTION

Methods of treatment which utilize the specific targeting and killing of cells having FGF receptors on their surfaces are herein provided. Of specific interest is the treatment of tumorigenic conditions in mammals by the administration of tumoricidal dosages of medicaments made from mitoxic FGF conjugates.

Evidence exists that several cancers, other than melanomas, including ovarian, pancreatic and some colon carcinomas, have receptors for bFGF. Testing with radioactive binding assays on a number of human carcinogenic cell lines isolated from human cancers demonstrated that many but not all of these cell lines bind $^{125}$I-FGF. Cytotoxic conjugates, in particular FGF conjugated with the saporin molecule (FGF-SAP), were found to be potent inhibitors of cell growth in vitro for each cell line expressing FGF receptors. When these cell lines were grown subcutaneously as solid tumor xenografts in nude mice, FGF-SAP conjugates showed rapid reduction in tumor volume in those cell lines which responded to in vitro treatment of the conjugate, often within 48 hours of administration. Dosages which were effective in tumor reduction proved non-toxic to test animals. Treatment of human patients would be similarly effected by administering a therapeutically effective amount of the FGF conjugate in a physiologically acceptable carrier. Specifically, in the treatment, the conjugates are used to target cytotoxic agents into human melanoma, ovarian carcinoma, teratocarcinoma, and neuroblastoma cells to inhibit the proliferation of such cells. The conjugates are also used to target FGF receptor-expressing cells in similar tumorigenic pathophysiological conditions.

Methods of treating mammals with these FGF conjugates are provided herein. These conjugates are shown to be effective against the tumors disclosed above, as well as against other tumorigenic pathophysiological conditions caused by a proliferation of cells which are sensitive to FGF mitogenic stimulation.

DETAILED DESCRIPTION OF THE PREFERRED EMBODIMENTS

Figure 1:
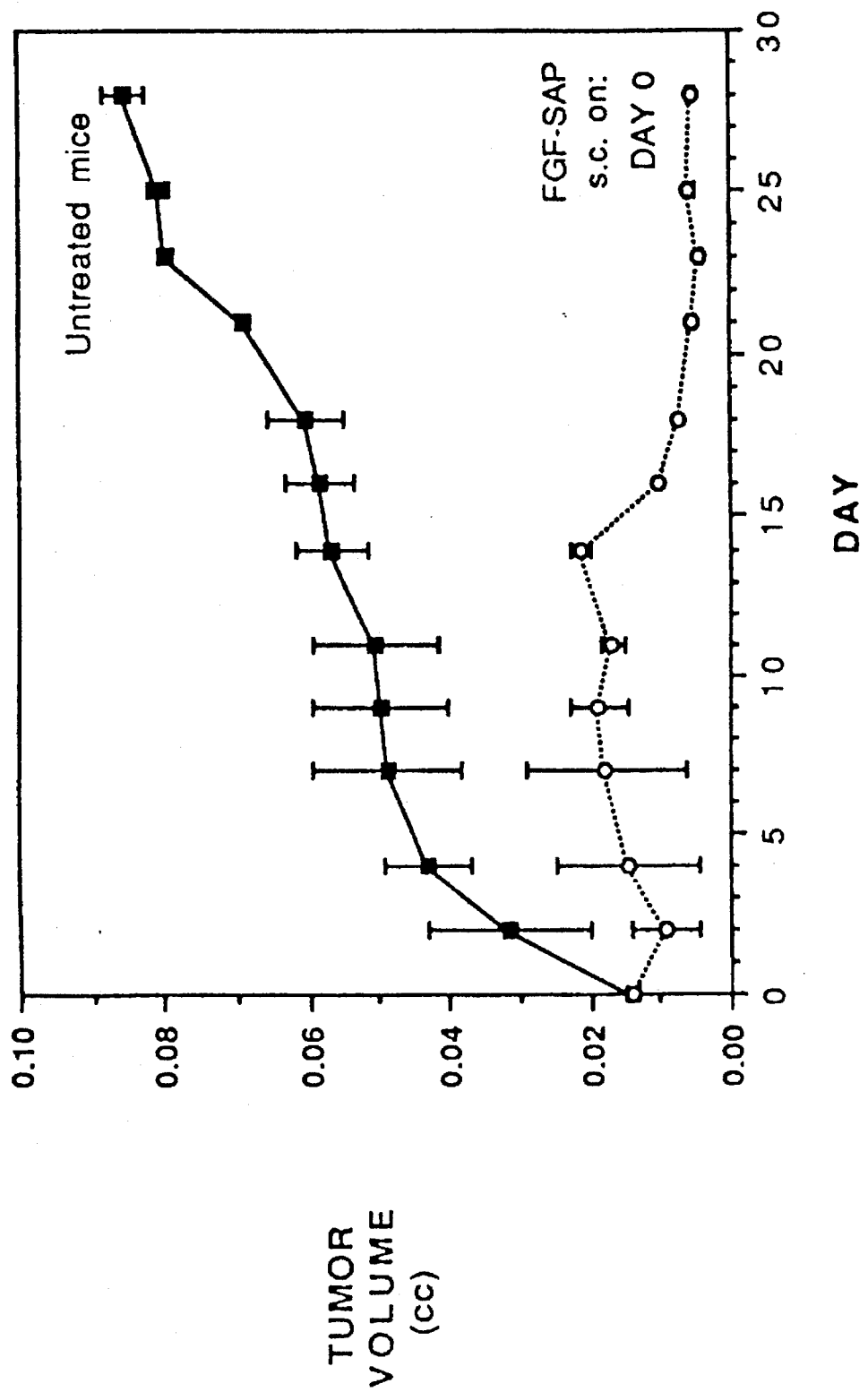
FIGS. 1 through 5 depict the results of the treatment of nude mice with bFGF-SAP conjugate, which mice had been injected with Mel Tang human melanoma cells.

The present invention comprises treatment using conjugates of a cytotoxic agent and an FGF polypeptide reactive with an FGF receptor, to inhibit growth and proliferation of FGF-sensitive cells in vitro and in vivo. FGF-conjugates are shown to be effective against tumorigenic pathophysiological conditions caused by a proliferation of cells which are sensitive to FGF mitogenic stimulation. Tumors against which FGF-conjugates are shown to be effective include but are not limited to human melanomas, human ovarian carcinomas, human teratocarcinomas, and neuroblastomas.

The conjugates employed comprise either basic FGF or another FGF polypeptide reactive with an FGF receptor, and a cytotoxic agent, particularly a ribosome-inactivating protein (RIP), such as saporin, although other cytotoxic agents can also be advantageously used. Basic FGF is preferably employed because of its commercial availability. The cytotoxic agent can be attached to FGF through a chemical bond, or the composition can be prepared as a chimera, using recombinant DNA techniques. In either case, the conjugate molecule is designed and produced in such a way that the receptor-binding epitope of the FGF moiety of the complex is left available for recognition by the FGF receptor.

Cytotoxic conjugates such as the FGF conjugate described herein offer advantages over immunotoxins. Cytotoxic conjugates may be administered locally directly to a tumor site. Cytotoxic conjugates can be chemically defined, synthesized and characterized, and prepared in large quantities using the techniques of recombinant DNA. Cytotoxic conjugates in general require a lower dosage to be effective than immunotoxins.

In addition to basic FGF (bFGF) and acidic FGF (aFGF), there are known to be a number of other proteins exhibiting FGF mitogenic activity mediated through binding to an FGF receptor. Mammalian basic FGF is a 146-residue peptide having a molecular weight of about 16 kD, and a pI of about 9.6, which may have an amino terminal extension. Other FGF proteins in addition to aFGF include HST, INT/2, FGF-5, FGF-6, and KGF(FGF-7), see Baird et al., *Brit. Med. Bull*, 45, 438–452 (1989). All induce mitogenic activity in a wide variety of normal diploid mesoderm-derived and neural crest-derived cells. One test of such "FGF mitogenic activity" is the ability to stimulate proliferation of cultured bovine aortic endothelial cells, as described in Gospodarowicz et al., *J. Biol. Chem.*, 257, 12266–12278 (1982) and Gospodarowicz et al., *P.N.A.S.*, 79, 4120–4124 (1976). The term "FGF" is generally used to refer both to proteins having amino acid sequences found in a mammalian host, as well as modified sequences, having amino acid substitutions, deletions, insertions or additions, which still express mitogenic activity, mediated through binding to an FGF receptor.

Purified preparations of bFGF and aFGF are frequently observed to include several molecular forms of the mitogens. It is understood that differences in amino acid sequences can occur in FGF from different species as well as between FGFs from individual organisms of species. The term is also intended to encompass both proteins isolated from natural sources as well as those made synthetically, as by recombinant means or possibly by chemical synthesis.

The amino acid sequence of an exemplary mammalian bFGF obtained from bovine pituitary tissue is reported in Esch et al., *P.N.A.S.*, 82, 6507–6511 (1985); it is also set forth in U.S. Pat. No. 4,956,455, issued Sep. 11, 1990, the disclosure of which is incorporated herein by reference. The term "bFGF" should be generally understood to refer to proteins or polypeptides having substantially the same amino acid sequence and mitogenic activity as that of bovine bFGF or human bFGF. cDNAs encoding human aFGF, see Jaye et al., *Science*, 233, 541–545 (1986); bovine bFGF, see Abraham et al., *Science*, 233, 545–548 (1986), human bFGF, see Abraham et al., *EMBO J.*, 2523–2528 (1986), and Abraham et al., *Quant. Biol.*, 51, 657–668 (1986), and rat bFGF, see Shimasaki et al., *B.B.R.C.* (1988) and Kurokawa et al., *Nucleic Acids Res.*, 16, 5201 (1988) have been cloned and sequenced; they predict the existence of proteins identical to bovine bFGF and aFGF found by protein sequencing.

As used herein, the term "FGF receptor" is used to refer to receptors which are able to bind basic FGF, or both basic and acidic FGF, or other proteins having FGF activity, and transport it into the cell. Included among these are the receptors described in T. Imamura, *B.B.R.C.*, 155, 583–590 (1988) and in Moscatelli, *J. Cell. Physiol.*, 131, 123–130 (1987). As used herein, the term "polypeptide reactive with the FGF receptor" refers to any polypeptide which is capable of binding an FGF receptor and of being transported into the cell thereby.

Basic FGF is commercially available, for example, from Amgen (Thousand Oaks, Calif.) and from Amersham International, and can be obtained from a variety of tissue types of mammals. Examples of methods of purifying basic FGF are reverse-phase high performance liquid chromatography (RP-HPLC) and heparin-Sepharose affinity chromatography.

Cation exchange HPLC and RP-HPLC are described in Bohlen et al, *P.N.A.S.*, 81, 5364–5368 (1984). purification by heparin-Sepharose affinity chromatography is disclosed in U.S. Pat. No. 4,785,079, as well as in Gospodarowicz et al., *P.N.A.S.*, 81, 6963–6967 (1984) and Gospodarowicz, *Meth. Enzym.*, 147, 106–119 (1987). In addition, bFGF can be synthesized, as by recombinant methods. Expression of a recombinant protein in yeast and *E. coli* is described in Barr et al., *J. Biol. Chem.*, 263, 16471–16478 (1988) and in U.S. Pat. No. 4,956,455.

The FGF-cytotoxic agent conjugate can be purified on a column containing immobilized heparin. Appropriate columns include heparin-Sepharose and heparin-agarose. The bound conjugate can be eluted with a Salt gradient, such as NaCl; it elutes between 1 and 3M NaCl.

FGF, conjugated to a cytotoxic agent, is used to target the cytotoxic agent to specific cells of interest. As used herein, the term cytotoxic agent refers to a molecule-capable of inhibiting cell function. The term includes agents which are only toxic when transported into the cell and also those whose toxic effect is mediated at the cell surface. A variety of cytotoxic agents can be used, particularly those which inhibit protein synthesis. As one example, bFGF is combined with a ribosome-inactivating protein (RIP) such as, for example, saporin-6 (SAP) or other SAP derivatives. SAP is a potent RIP which is isolated from the seeds of the plant *Saponaria officinalis*, see Stirpe et al., *Biochem J.*, 216, 617–625 (1983). Conjugation of FGF with SAP has the advantage that SAP need not be modified to prepare it for conjugation. This is in contrast to other cytotoxic agents which must be extensively modified to be put in appropriate form for cytotoxic targeting. Other appropriate cytotoxic agents include, but are not limited to, ricin, ricin A chain, gelonin, diphtheria toxin, diphtheria toxin A chain, pokeweed antiviral protein (PAP), and Pseudomonas exotoxin. Alternatively, it may be feasible to use a drug as the cytotoxic agent; examples of such drugs include anthracyclines, such as the daunomycins (including daunorubicin and doxorubicin) and methotrexate and its analogs.

FGF is suitably conjugated to a protein cytotoxic agent by known chemical reactions, such as through derivatization with a reactive sulfhydryl-containing moiety, such as SPDP, or via a cross-linking agent, such as glutaraldehyde or carbodimide. For example, the cytotoxic agent may be derivatized with a reactive sulfhydryl containing agent, such as N-succinimidyl-3(2-pyridyldithio)propionate, before FGF is added and mixed therewith. The FGF conjugate can be separated from the unreacted products on a suitable column. Alternatively, bFGF can be conjugated to a drug, such as 14-bromo doxorubicin through the sugar moiety, as by the cisaconitase method, see Shen and Riser, *B.B.R.C.*, 102, 1048 (1981).

Alternatively, chimeric FGF-conjugates can be prepared by recombinant methods. Such methods as applied to conjugates of IL-2 or TGFα are described in Chaudhary et al., *P.N.A.S.*, 84, 4538–4542 (1987) and in Lorberman-Galski et al., *P.N.A.S.*, 85, 1922–1926 (1988). See also Maniatis et al., *Molecular Cloning: A Laboratory Manual*, Cold Spring Harbor Laboratory (1982).

A conjugate containing FGF and a cytotoxic agent may be useful in treating a variety of FGF-mediated pathophysiological conditions. As used herein, the term "FGF-mediated pathophysiological condition" refers to a deleterious condition characterized by or caused by proliferation of cells which are sensitive to bFGF mitogenic stimulation; of particular interest are such tumorigenic conditions.

The following examples are intended to illustrate the production and use of FGF-conjugates but should be understood as not limiting the invention.

EXAMPLE I

CONJUGATION OF bFGF WITH SAPORIN

Recombinant bFGF corresponding to the sequence of 154 amino acids disclosed in Abraham et al., *Ouant. Biol., 51*, 657–668 (1986) was obtained from Farmitalia Carlo Erba. Saporin-6 was purified according to the method of Stirpe et al., supra, as modified by Lappi et al., *B.B.R.C.*, 129, 934–942 (1985). Briefly, seeds of *Saponaria officinalis* were extracted by grinding in 0.14M NaCl in 5 mM sodium phosphate buffer, pH 7.2 (8 ml/g). After overnight stirring at 4° C., extracts were strained through cheese-cloth and were centrifuged at 28000 g for 30 minutes. The supernatant was separated from the sediment and from floating fat; it is referred to as "crude extract".

Crude extracts were dialyzed against 5 mM sodium phosphate buffer, pH 6.5, centrifuged at 28000 g for 30 minutes and applied to a CM cellulose column (CM 52; Whatman, Maidstone, Kent, U.K.), which after washing, was eluted with a 0–0.3M NaCl gradient in the same buffer. This material was then dialyzed against water and chromatographed on an FPLC Mono S column (Pharmacia, Uppsala, Sweden) equilibrated with 50 mM sodium borate pH 9.5, 0.156M sodium chloride. The protein was eluted with a 20 minute gradient from 0.156M to 0.186M sodium chloride. The resultant peak material was then extensively dialyzed against Milli-Q water (Millipore, Bedford, Mass.). A portion of the dried material was weighed and dissolved in water at a concentration of 1 mg/ml. An ultraviolet spectrum was recorded giving a 1% extinction coefficient of 6.4 at 277 nm, the absorbance maximum. At 280 nm the $E_{280}$ was 6.0. Protein assay using the Lowry method, Lowry et al., *J. Biol. Chem.*, 193, 265–275 (1951), using BSA as a standard gave a result of 1.07 mg/ml.

SAP was derivatized with N-succinimidyl-3(2-pyridyldithio)propionate (SPDP; Pharmacia Fine Chemicals, Piscataway, N.J.) according to the manufacturer's instructions. Briefly, SAP was dissolved in (2.7 mg/mL) in sodium phosphate buffer (0.1M, pH 7.5) containing NaCl (0.1M). A 1.25 molar excess of SPDP, dissolved in ethanol, was added by drop while stirring, and allowed to react for 30 minutes at 23° C. with occasional stirring. Excess reagent and low molecular weight reaction products were removed by gel filtration. bFGF (2 mg/ml) was added to and mixed with the derivatized saporin (6 mg/ml in 0.1M sodium phosphate, 0.1M sodium chloride, pH 7.5) for two hours at room temperature. The reaction was terminated by the addition of 35 µL of 0.1M iodoacetamide. After an additional 30 minutes, the reaction mixture was diluted to 30 ml and loaded onto a heparin-Sepharose (Pharmacia) column (0.5×5.5 cm). The bound proteins were eluted with a step gradient of 0.6M, 1M and 2M NaCl in 10 mM TRIS, pH 7.4. The material eluting between 1M and 2M was pooled. Final purification of the conjugate was achieved after the pool was dialyzed against water and chromatographed on a Mono 5 NaCl Cation exchange column (Pharmacia) (buffer A: 50 mM sodium borate, pH 8.0, buffer B:0.5M NaCl in buffer A). Fractions containing the conjugate were detected by silver staining after PhastGel (Pharmacia) electrophoresis, and appropriate fractions were pooled for analysis.

Synthesis of the conjugate was assessed by gel electrophoresis and allowed to proceed until no detectable bFGF remained in the reaction mixture. Chromatographic separation on heparin-Sepharose and subsequent electrophoretic analysis of each of the peak fractions showed that, while SAP does not bind to heparin-Sepharose, the conjugate does. Only small amounts of the conjugate were released during the 1.0M NaCl wash; the major product eluted with the 2M wash and contained equimolar amounts of SAP and basic FGF (Mr-40,000). However, there was also a portion of the conjugate that has an estimated Mr>68,000, presumably as a result of the conjugation of two molecules of bFGF per molecule of saporin.

Unambiguous identification of the SAP-FGF conjugate was accomplished using sequence specific antisera raised in rabbits. The immunogen used was a fragment of bFGF comprising amino acids 1 through 24, chemically synthesized using a Beckman 990 Peptide Synthesizer. Western blot analysis showed that all molecular weight forms of the conjugate contained both bFGF and SAP The antiserum recognizes the mid-portion of the peptide and cross-reacts on equimolar basis with purified bovine and recombinant human basic FGF.

Samples in a sodium dodecyl sulfate-containing polyacrylamide gel, after electrophoresis, were electro-blotted onto nitrocellulose membranes and allowed to air dry. The membrane was covered with TRIS-buffered saline (TBS) and agitated for 10 minutes. The solution was aspirated and discarded. The membrane was covered with 5% nonfat milk (NFM) in TBS and agitated for 10 minutes. The solution was aspirated and discarded. Primary antibody, either anti-SAP or anti-bFGF anti-serum, at a concentration of 1/1000 in NFM/TBS was added and agitated overnight. The solution was aspirated and discarded. The membrane was covered with TBS, agitated for 10 minutes and the solution aspirated and discarded. The membrane was covered with 0.05% NP40/TBS and shaken 1 minute; the solution was aspirated and discarded. The final TBS and NP40/TBS washes were repeated twice. Horseradish peroxidase labeled anti-IgG at a dilution of 1/2000 in NFM/TBS was added, and the membrane was agitated for 2 hours. The TBS and NP40/TBS wash steps were repeated. The membrane was placed in a freshly mixed solution of 60 mg of 4-chloro-1-naphthol in 20 mL methanol, 100 mL double-distilled water and 60 µL 30% $H_2O_2$, and the solution was added to the membrane and allowed to develop. The solution was aspirated and discarded and the reaction stopped by rinsing with water. The membrane was allowed to dry.

EXAMPLE II

ACTIVITY OF THE FGF/SAP CONJUGATE

The capacity of the conjugate to recognize the basic FGF receptor was examined in BHK cells using the procedure described in Moscatelli, D., *J. Cell Physiol.* 131, 123–130(1987). Briefly, cells were grown to subconfluence and incubated in 300 µL buffer containing F-12 14 mM $NaHCO_3$, 25 mM HEPES and 0.2% gelatin at 4° C. for two hours with 10 µL radioiodinated bFGF in the presence of various concentrations of bFGF or the conjugate. The cells were then washed three times with 0.5 mL phosphate-buffered saline (PBS), and twice with 2M NaCl in PBS. Binding to the high affinity receptor was determined by counting the membrane fraction that was solubilized in 0.5% Triton X-100 in PBS (pH 8.1).

The protein synthesis inhibitory activity of the SAP protein was compared to the protein synthesis inhibitory activity of the bFGF-SAP conjugate in in vitro assays of protein synthesis as described in Siena et al., *Blood*, 72, 756–765 (1988). The cytotoxic activity of the conjugate was tested on baby hamster kidney fibroblasts (ATCC Accession No. CRL 6281). BHK cells were plated in 24 well plates at a concentration of 5000 cells/ml and incubated overnight at 37° C., 5% CO2. The following morning HEPES-buffered DMEM and F-12 media (1:1) plus 5% FCS was aspirated from the wells and replaced with media alone or with media containing the conjugate, basic FGF or saporin. Two days later, the cells were washed twice and trypsinized, and cell numbers were determined with a Coulter Particle Counter (Coulter Electronics, Hialeah, Fla.).

It was shown that the conjugate retains saporin activity when tested in an in vitro protein synthesis inhibition assay. The conjugate, as expected, is slightly less active (about two-fold) than free SAP. This is consistent with the low level of derivatization of SAP prior to the conjugation (0.8 moles SPDP/mole) and with probable steric hindrance due to the presence of bound bFGF. In contrast, the results obtained in the radioreceptor assays for bFGF show that the bFGF-SAP is equipotent to if not slightly more active than, bFGF in the binding assay. Thus, it appears that the commitment of free sulfhydryl groups in bFGF to bridging with SAP does not interfere with its capacity to recoginze and bind to its receptor; if anything, this reaction may stabilize bFGF.

Basic FGF-SAP is a potent cytotoxic factor for BHK cells; however, SAP alone has no toxic effect on these cells even at the highest dose tested ($10^{-8}$M), and bFGF alone has a slight inhibitory effect on proliferation. A mixture of bFGF and SAP had a slight toxicity but only at the highest concentration tested. The $IC_{50}$ (25 pM) for the cytotoxic agent compares well with the potency of bFGF (15 pM) in proliferation assays. Specificity of the cytotoxic agent was examined in competition experiments in an effort to establish that the mitotoxic activity of the conjugate is receptor specific. BHK cells were preincubated for one hour with various levels of bFGF or nerve growth factor (NGF) which does not bind FGF receptors, prior to treatment of the cells with the cytotoxic agent. It was also shown that there is a dose-related inhibition of the cytotoxic activity in the presence of increasing amounts of basic FGF. In contrast, a thousand-fold excess of NGF has no effect.

FGF-conjugates have a striking effect on certain tumorigenic FGF-mediated pathophysiological conditions. In some instances, this is considered to be a consequence of FGF's role in angiogenesis, and the presence of FGF receptors in relevant tissues. The effectiveness of FGF-conjugates is illustrated in Examples III and IV.

EXAMPLE III

INHIBITION OF ANGIOGENESIS IN RABBIT CORNEA

Elvax (ethylene-vinyl acetate copolymer resin, Dupont, Wilmington, Del.) pellets were produced in the following manner. About 60 mg of washed and dried Elvax was dissolved in 500 µL of methylene chloride. This was added to 50 µg of dried bFGF. 5 µL drops were dropped onto a slide frozen in dry ice. Pellets were left in the freezer overnight and then dried in a desiccator.

New Zealand white rabbits were anaesthetized with Innovar Vet: 1 mL/kg. An incision was made in the cornea of the rabbit eye, and a pocket was opened with a spatula or forceps. One pellet was inserted in the pocket. Pellets were inserted in both eyes. The eye was washed with saline, and 1 ml of gentamicin was injected intramuscularly. The rabbit was left for five days, and angiogenesis was observed. After five days, each left eye was treated with 20 µL of 100 ng bFGF-SAP prepared as in Example I in 0.25% BSA. The right eyes were treated with 20 µL of 0.25% BSA alone. The treatment was done twice daily by dropping the solution as eye drops onto the cornea of the rabbit. The person treating the animals was unaware of the identity of the samples. After 10 days, the animals were evaluated for angiogenesis of the cornea by microscopic analysis by an evaluator who did not know the treatment regimen, and anglogenesis was judged, with +++ indicating maximal angiogenesis and—indicating no anglogenesis.

The results are provided in Table 1. As can be seen, angiogenesis in corneas treated with bFGF-SAP was markedly reduced over that of controls.

TABLE 1

| ANIMAL | RIGHT EYE | LEFT EYE |
| --- | --- | --- |
| 995 | + | − |
| 997 | +++ | + |
| 998 | +++ | + |
| 999 | ++ | − |

EXAMPLE IV

EFFECT OF FGF-SAP DUPUYTREN'S CELL

Cells obtained from surgical removal of tissue from the hand of adult patients diagnosed as having Dupuytren's Contracture, a malady effecting movement of the hand, were placed in primary culture. These cells have between 10,000 and 15,000 basic FGF receptors per cell.

The cells were grown overnight in a 24-well tissue culture dish at a concentration of 10,000 cells per well in HEPES-buffered Dulbecco's Minimal Eagles Medium (DMEM) with 10% Fetal Calf Serum (FCS). The next morning, the media was removed and replaced with media containing concentrations of bFGF-SAP conjugate ranging from $10^{-8}$ to $10^{-12}$ molar. Controls included wells treated with media only, wells treated with similar concentrations of basic FGF alone, saporin alone, and basic FGF and saporin together but not conjugated. The cells were returned to the incubator for 72 hours. At the end of this incubation, the cells were washed, removed with trypsin and counter on a Coulter cell counter. The number of cells in the media controls was compared with the number of cells in the treated wells. The $IC_{50}$, the concentration at which 50% of the cells have been killed, is calculated for FGF-SAP. The results of these cell killing assays show that Dupuytren's cells are sensitive to basic FGF-SAP, with the number of cells killed being proportional to the dosage of FGF-SAP. Substantially higher concentrations of either SAP or FGF+SAP were needed to achieve the same results, and the number of cells killed, particularly for SAP alone, was not as clearly dose-dependent. Similar results were obtained with three other cell samples.

It has been found that FGF-cytotoxic conjugates can be used to target the cytotoxic agent to cells expressing FGF receptors with the objective of causing cell death. Tests have now shown that there is a direct relationship between the number of FGF receptors per cell and the dose at which 50% of such cells are killed (the $IC_{50}$). The toxicity of bFGF-SAP was determined for each cell line after 48 or 72 hours exposure to bFGF-SAP. Cell numbers were determined, and the concentration that reduced the number of cells by 50% was plotted against receptor number for that cell line. Receptor number was determined by the method of Moscatelli, D., *J. Cell. Physiology,* 131, 123–130 (1987). For cells known to have extremely high receptor numbers, for example, BHK cells, the $IC_{50}$ is identical to the affinity constant of basic FGF for its receptor (both are about 25 pM for BHK cells). This unexpected result indicates that the presence of the cytotoxic agent, even such a large molecule as SAP, does not reduce the FGF activity of the conjugate. These test results appear to indicate that these cell lines which are expressing a large number of FGF receptors are more sensitive to the conjugate than those expressing a much lower number.

Cell lines may be tested for the presence of FGF receptors by $^{125}$I-FGF binding assays, for example. This assay is presented in Example V. It can not be known a priori what cell lines will carry FGF receptors.

A number of cell lines originating from human cancers have now been tested for the presence of FGF receptors. The cell lines tested include SK-Mel-1, a human melanoma, SK-N-MC, a human neuroblastoma, and PA-1 a human ovary teratocarcinoma cell line, and A431, a human epidermoid carcinoma. These lines were obtained from the American Type Culture Collection, Rockville, Md.). FSaIIC, a murine fibrosarcoma, obtained form Dr. Beverly Telchef of the Dana Farbaer Cancer Institute, Boston, was also tested. Other cell lines may be similarly tested.

EXAMPLE V

$^{125}$I-FGF RECEPTOR BINDING ASSAY

Cells were seeded in 12-well tissue culture plates (Costar) at $10^5$ cells/well and grown until confluent in their respective medium. SK-Mel-1, SK-N-MC, and PA-1 are grown in modified Eagle's medium (MEM) supplemented with 10% Fetal Calf Serum (FCS). FSaIIC was grown in α-MEM with 5% FCS. A431 is grown in RPMI 1640 medium supplemented with 10% FCS. $^{125}$I-FGF binding was performed using a radioreceptor assay as described in Neufeld, G. et al. Identification of the fibroblast growth factor receptor in human vascular endothelial cells. *J. Cell Physiol.,* 136: 537–542, 1991. Briefly, cell monolayers were incubated with fresh, unsupplemented medium containing 0.2% gelatin and 3 µg/ml heparin (Sigma) for 1 hr. at 37° C./5% $CO_2$, and then washed with ice-cold medium and allowed to cool for 1 minute. Cells were incubated with various concentrations of $^{125}$I-FGF in 250 µl of the same medium for 2 hours on ice. The cells were then gently washed twice with ice cold 0.9% phosphate buffered saline (PBS) to remove unbound $^{125}$I-FGF, and remaining cell-associated radioactivity was extracted with 1% Triton X-100 and quantitated using a Beckman Gamma Counter. Non-specific binding was determined by inhibiting specific binding using a 200-fold excess of non-radiolabeled FGF.

The results of these studies are that SK-Mel-1, PA1, SK-N-MC and FSaIIC cells expressed high affinity FGF receptors, that is receptors that bind both basic and acidic FGF, but preferentially bind basic FGF. Unexpectedly, it was found that A431 cells were devoid of FGF receptors.

The SK-Mel1, PA-1, SK-N-MC, FSaIIC, and A431 cell lines were tested in vitro to determine cell survival when treatment with both FGF-SAP and SAP alone. Correlations between cell survival and the presence of FGF receptors as determined in Example V can then be determined. The experimental procedure and results for in vitro cell testing are set forth in Example VI.

EXAMPLE VI

IN VITRO CELL SURVIVAL STUDIES

Cells were plated in 96-well tissue culture plates (Costar) at $10^3$ cells/well in their respective medium. One day later, the medium was removed and medium containing 1 pM to 1 µM of the conjugate FGF-SAP or free SAP. Cells were treated in triplicate and maintained at 37° C./5% $CO_2$. Seventy-two hours after the treatment was initiated, the medium was removed and the cells were trypsinized and counted using a Coulter counter (Coulter Electronics, Inc., Hialeah, Fla.). Results are expressed as the mean cell number from treated wells, normalized to media controls, as a function of the FGF-SAP or SAP concentration. $IC_{50}$ values were calculated from dose response curves and represent the concentration of FGF-SAP or SAP which resulted in a 50% reduction in cell number.

It was determined that FGF-SAP is a potent inhibitor of cell growth for each of the cell lines expressing FGF receptor, as is shown in Table 2. In contrast, it can be seen from Table 2 that FGF-SAP demonstrated minimal cytotoxic effects in A431 cells. SAP-associated growth inhibition was observed for PA-1 and SK-N-MC cells, but only after exposure to SAP concentrations that were 2–6 orders of magnitude greater than the conjugate. The addition of FGF and SAP in a non-covalent mixture had no cytotoxic effects.

Additional cells lines also showed inhibition of vitro growth after treatment with a bFGF-SAP conjugate for 72 hours. These include human melanoma cell lines SK-MEL 24 and SK-MEL 5 (both on deposit and available from the American Type Culture Collection, ATCC) and the human ovarian carcinoma cell line SKOV-3, also available from the ATCC. In Vitro and in vivo testing was done using parental type Mel Tang cells, available from the Roger Williams Cancer Center at Brown University, Providence, R.I., and is discussed in Examples IX and X below.

TABLE 2

High affinity FGF receptor number, FGF dissociation constant, and growth inhibition of tumor cell lines in the presence of FGF-SAP or SAP

| Cell Line | $Kd^a$ | FGF-R Number | bFGF-$SAPIC_{50}^b$ | $SAPIC_{50}^b$ |
|---|---|---|---|---|
| Sk-Mel-1 | 167 | 19,000 | 0.1 | No effect |
| PA-1 | — | 33,000 | 1.0 | 500 |
| SK-N-MC | — | 45,000 | 0.01 | 1000 |
| FSaIIC | 41 | 7,000 | 2.5 | No effect |
| A431 | $NA^c$ | 0 | No effect | No effect |

$^a$Kd, in pM
$^b$IC50, in nM, represents the concentration calculated from dose response curves which resulted in a 50% reduction in cell number. Each value is the mean of at least three determinations.
$^c$NA = not applicable It is possible to test in vivo the cancerous cell lines tested in vitro by methods known in the art. This is accomplished by subcutaneously implanting the desired tumor cells in immunodeficient nude mice to create a xenograft in the test animal. The animals having the tumors are then treated according to various methods with a range of dosages of an FGF-cytoxic conjugate, equivalent dosages of cytotoxin, and various other controls. Appropriate dosage ranges of FGF-conjugate can be initially determined by lethal dose determinations ($LD_{50}$) of the conjugates in BALB/c mice. In vivo studies using FGF-SAP, for example, are described in Example VII below.

EXAMPLE VII

IN VIVO ANTITUMOR STUDIES USING NUDE MICE

Experiments with SK-Mel-1, SK-N-MC, and A431 cell lines were performed in 8–10 week old male nu/nu mice while those with PA-1 cells used 8–10 week old female nu/nu mice. Nude mice were bred and maintained by the Roger Williams Hospital Animal Care Facility. FSaIIC cells were carried in 8–10 week old male C3H/HeN mice (Taconic Laboratories, Germantown, N.Y.). The $LD_{50}$ of FGF-SAP in BALB/c mice was found to be 500 µg/kg, with toxicity manifested as extensive hemorrhage, often in the intestinal tract. Lappi, D. A. et al. Basic fibroblast growth factor-saporin mitotoxin: An endothelial cell growth inhibitor. *J. Cell. Biochem., Suppl.*, 14E: 222, 1990. For in vivo studies, groups of 5 mice were inoculated with $2 \times 10^6$ tumor cells subcutaneously in the right rear flank. In the initial studies, 125 µg/kg FGF-SAP or 85 µg/kg SAP (that is, equivalent molecular concentrations of saporin in each treatment group), was dissolved in sterile PBS, and was administered as a single intravenous injection via tail vein 0, 1, 5, 10 or 15 days after tumor implantation. In subsequent studies, mice received a course of intravenous injections of 0.5 µg/kg FGF-SAP administered at weekly intervals, for a total of 4 doses. The progress of each tumor was measured at least twice weekly, beginning five days after tumor implantation, and tumor volumes were calculated using the formula: Volume=[(minimum measurement)$^2$ (maximum measurement)]÷2. Results are expressed as mean tumor volumes of treated groups, normalized to untreated controls, as a function of time. Errors are standard errors of means. Statistical comparisons of mean tumor volumes for the various treatment groups were made using Student's t-test (Statview SE, Brainpower, Calabasas, Calif.).

Preliminary toxicologic evaluation of FGF-SAP showed a dose of 500 µg/kg to be lethal in BALB/c mice (Lappi et al. *J. Cell. Biochem., Suppl.*, 14E: 222 (1990)) and 250 µg/kg to be non-lethal. Accordingly, 125 µg/kg was chosen as an initial dose of FGF-SAP. Pilot studies were performed in nude mice bearing human tumor xenografts in which a single intravenous dose of FGF-SAP was administered 1, 5, 10, or 15 days after tumor implantation. FGF-SAP caused rapid reductions in tumor volume, often within 48 hours of administration, and in some animals, complete tumor regression was observed. Transient reductions in tumor size were observed even when treatment was delayed until day 15, when tumor volumes were approximately 50–100 mm$^3$. By day 30, however, mean volumes of tumors in treated mice measured only 5–33% of control tumors. Since FGF-SAP at this dose level appeared equally efficacious when administered on day 1, 5, or 10, day 5 was chosen as the treatment day for further investigations. At this time, tumors are approximately 40–50 mm$^3$ in volume.

The next series of studies compared the broad range of FGF-SAP doses with equivalent doses of SAP to determine in vivo dose responses. Mean tumor volumes on day 30 for FGF-SAP or SAP-treated xenografts compared to untreated controls are displayed in Table 3. Studies performed in nude mice bearing PA-1, SK-N-MC, or SK-Mel-1 xenografts demonstrated growth inhibition with FGF-SAP and lack of efficacy using free SAP (Table 3). Antitumor responses to FGF-SAP were also observed in immunocompetent host mice bearing FSaIIC xenografts although FGF-SAP's effects were characteristically short-lived in this single dose regimen. No growth inhibition was observed in mice bearing A431 xenografts following treatment with FGF-SAP or SAP.

TABLE 3

Dose efficacy of FGF-SAP versus SAP administered as a single intravenous injection 5 days after tumor implantation in mice[a]

| Dose | | Mean Tumor Volume on Day 30 (% of Control)[b] | | | | |
|---|---|---|---|---|---|---|
| | (µg/kg) | SK-Mel-1 | PA-1 | SK-N-MC | FSaIIC | A431 |
| bFGF-SAP | 125.0 | 39 ± 14[c] | 32 ± 8[c] | 31 ± 15[c] | 83 ± 13 | 150 ± 26 |
| SAP | 85.0 | 118 ± 22 | 103 ± 5 | 90 ± 7 | 105 ± 0 | 128 ± 5 |
| bFGF-SAP | 0.5 | | 61 ± 19 | | | |
| SAP | 0.3 | | 92 ± 9 | | | |
| bFGF-SAP | 0.025 | | 71 ± 15 | | | |
| SAP | 0.017 | | 100 ± 3 | | | |

[a]$2 \times 10^6$ tumor cells were inoculated subcutaneously in the right rear flank of host mice.
[b]Mean tumor volumes for treated xenografts were calculated using 2–11 mice per treatment group. There were 2–24 mice in the control groups. Errors are standard errors of means.
[c]Significant difference between treatment and control tumor volumes, $p \leq 0.01$.

In conjunction with the evaluation of lower FGF-SAP doses in vivo, studies were performed in which multiple doses of FGF-SAP were administered intravenously. Only transient reduction in tumor volume and subsequent rapid tumor progression were observed with FGF-SAP at a single dose of 0.5 µg/kg as seen in Table 3. Therefore, groups of mice bearing SK-Mel-1, PA-1, SK-N-MC, or FSaIIC xenografts were treated with FGF-SAP (0.5 µg/kg) beginning on day 5, and then once a week for a total of four doses. Table 4 compares mean tumor volumes for the multiple low-dose FGF-SAP regimen to volumes for the single high dose regimen. Significant tumor reductions were observed on day 35 for each of the tumor types examined using the multiple low-dose treatment. This potent antitumor effect was not consistently observed with the single high-dose treatment.

TABLE 4

Comparison of FGF-SAP treatment regimens in tumor-bearing mice[a]

| | | Mean Tumor Volume (% of Control)[b] | |
|---|---|---|---|
| Cell Line | Day | Single High Dose[c] | Multiple Low Doses[d] |
| SK-Mel-1 | 12 | 38 ± 12[e] | 68 ± 12 |
| | 35 | 26 ± 7[e] | 11 ± 2[e] |
| PA-1 | 12 | 54 ± 10[e] | 72 ± 13 |
| | 35 | 56 ± 11 | 19 ± 6[e] |
| SK-N-MC | 12 | 58 ± 11 | 84 ± 5 |
| | 35 | 30 ± 11[e] | 18 ± 7[e] |
| FSaIIC | 12 | 34 ± 12[e] | 51 ± 3[e] |
| | 35 | 92 ± 18 | 42 ± 4[e] |

[a]$2 \times 10^6$ tumor cells were inoculated subcutaneously in the right rear flank of host mice.
[b]Mean tumor volumes were calculated using 2–14 mice per treatment group. There were 2–24 mice in the control groups. Errors are standard error of means.
[c]A single dose of FGF-SAP 125 µg/kg was administered on day 5.
[d]A dose of FGF-SAP 0.5 µg/kg was administered on day 5, followed by weekly injections for a total of 4 doses.
[e]Statistical difference between treatment and control tumor volumes, $p \leq 0.01$ It can be concluded, as demonstrated in Examples V through VII, that cytotoxins, in particular the ribosome-inactivating protein saporin, covalently linked to FGF exerts potent cytotoxic effects in vitro against a variety of tumor cell types expressing cell surface receptors for FGF. The in vitro data accurately predicts the superior cytotoxicity of FGF-SAP as compared with free SAP for FGF-receptor-bearing SK-Mel-1, PA-1 and SK-N-MC xenografts (Table 2) and the absence of significant antitumor effects on A431 xenografts.

The efficacy of FGF-SAP administered as multiple low doses in vivo is particularly impressive. This regimen affords the advantage of delivering repeated, relatively non-toxic FGF-SAP doses to tumor cells that survive the initial treatment. From a therapeutic standpoint, it is of great practical importance that more than one dose of conjugate may be administered with safety.

In vivo testing was also done using parental type Mel Tang cell line, available from the Roger Williams Cancer Center at Brown University, Providence, R.I. In vitro testing on this cell line was previously performed according to Example VI. In vitro growth of this cell line was dramatically inhibited by treatment with FGF conjugates, in particular FGF-SAP, when treated with the conjugate for 72 hours. The $IC_{50}$ was calculated to be 1 pM for this cell line.

EXAMPLE IX

INTRAVENOUS INJECTION OF FGF-SAP CONJUGATE

The following experiment was carried out so as to assess the effect of FGF-SAP administration upon tumor volume at the initial site of subcutaneous injection of Mel Tang cells in nude mice. Parental Type Mel Tang cells are a human melanoma cell line which may be obtained from the Roger Williams Cancer Center at Brown University, Providence, R.I. The following protocol was carried out wherein subcutaneous injection of Mel Tang cells was either accompanied by, or followed by the injection of the bFGF-SAP conjugate.

TABLE 5

| NUMBER OF MICE | TUMOR CELL INJECTION ($2 \times 10^6$ cells) | FGF-SAP INJECTION (0.125 mg/kg) |
|---|---|---|
| 5 | SQ, Day 0 | None |
| 5 | SQ, Day 0 | SQ, Day 0* |
| 5 | SQ, Day 0 | IV, Day 1 |
| 5 | SQ, Day 0 | IV, Day 5 |
| 5 | SQ, Day 0 | IV, Day 10 |
| 5 | SQ, Day 0 | IV, Day 15 |
| | Autopsy | Day 90 |

*FGF-SAP is mixed with cell suspension and injected simultaneously

Figure 2:
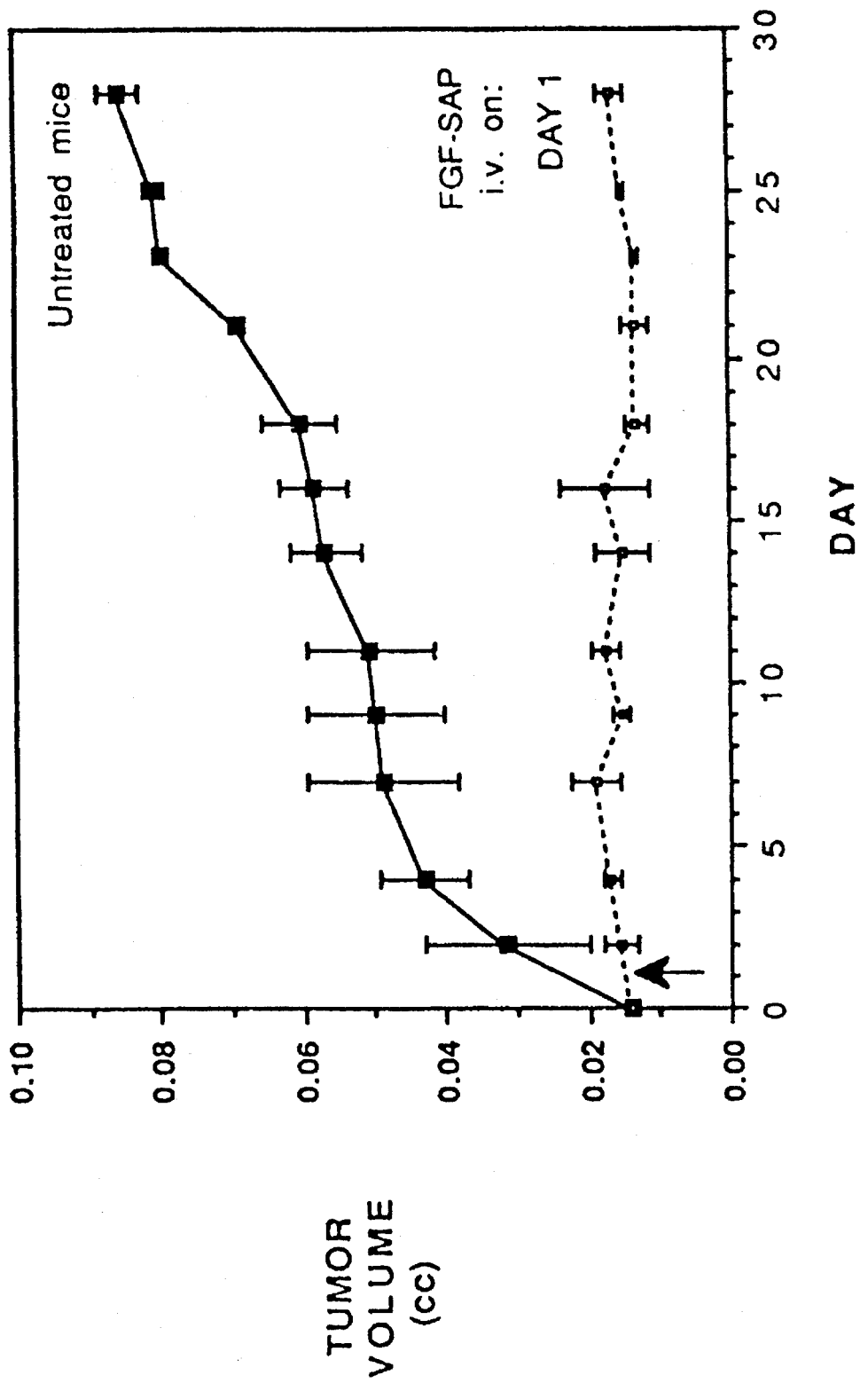
Figure 3:
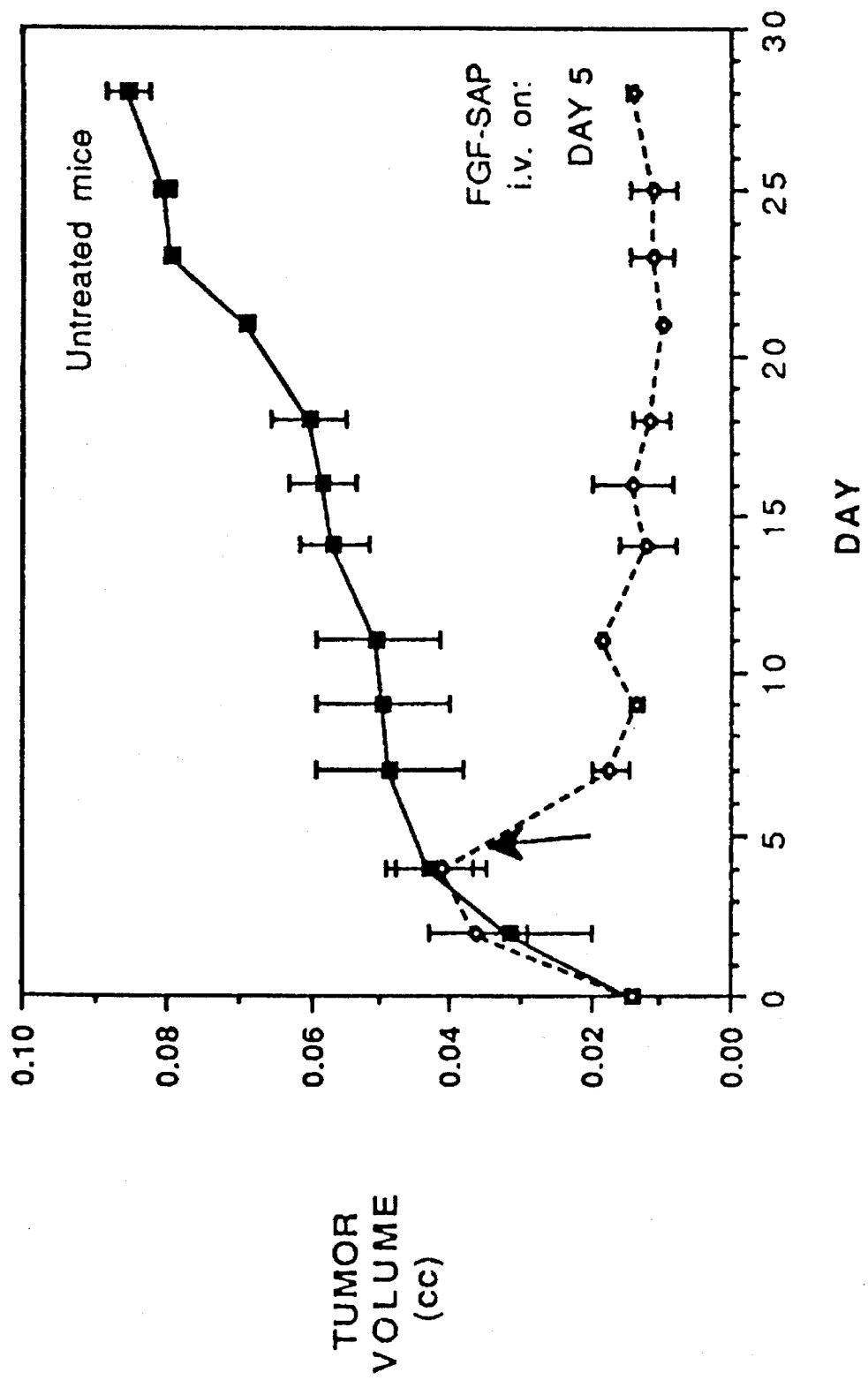
Figure 4:
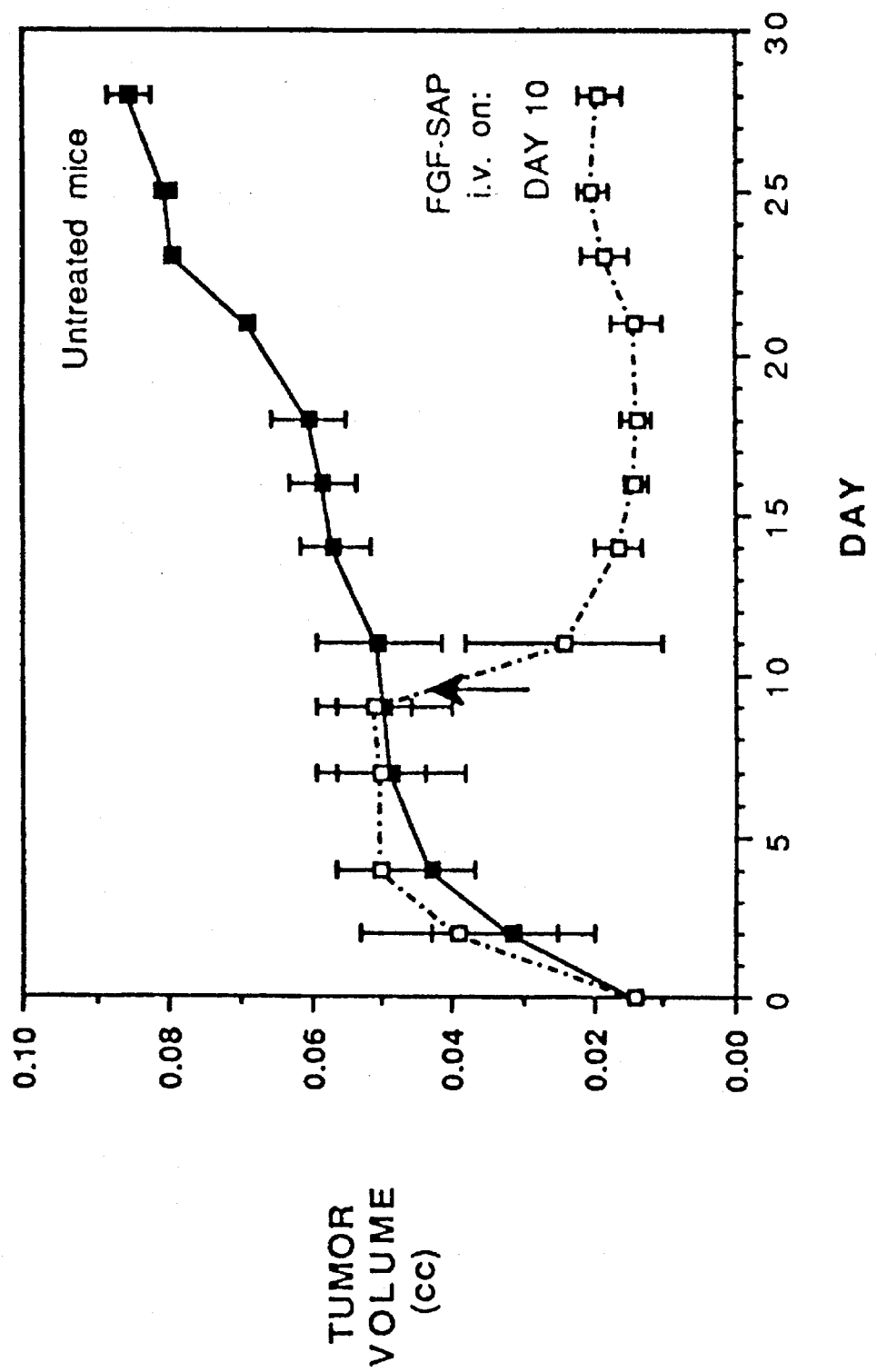
Figure 5:
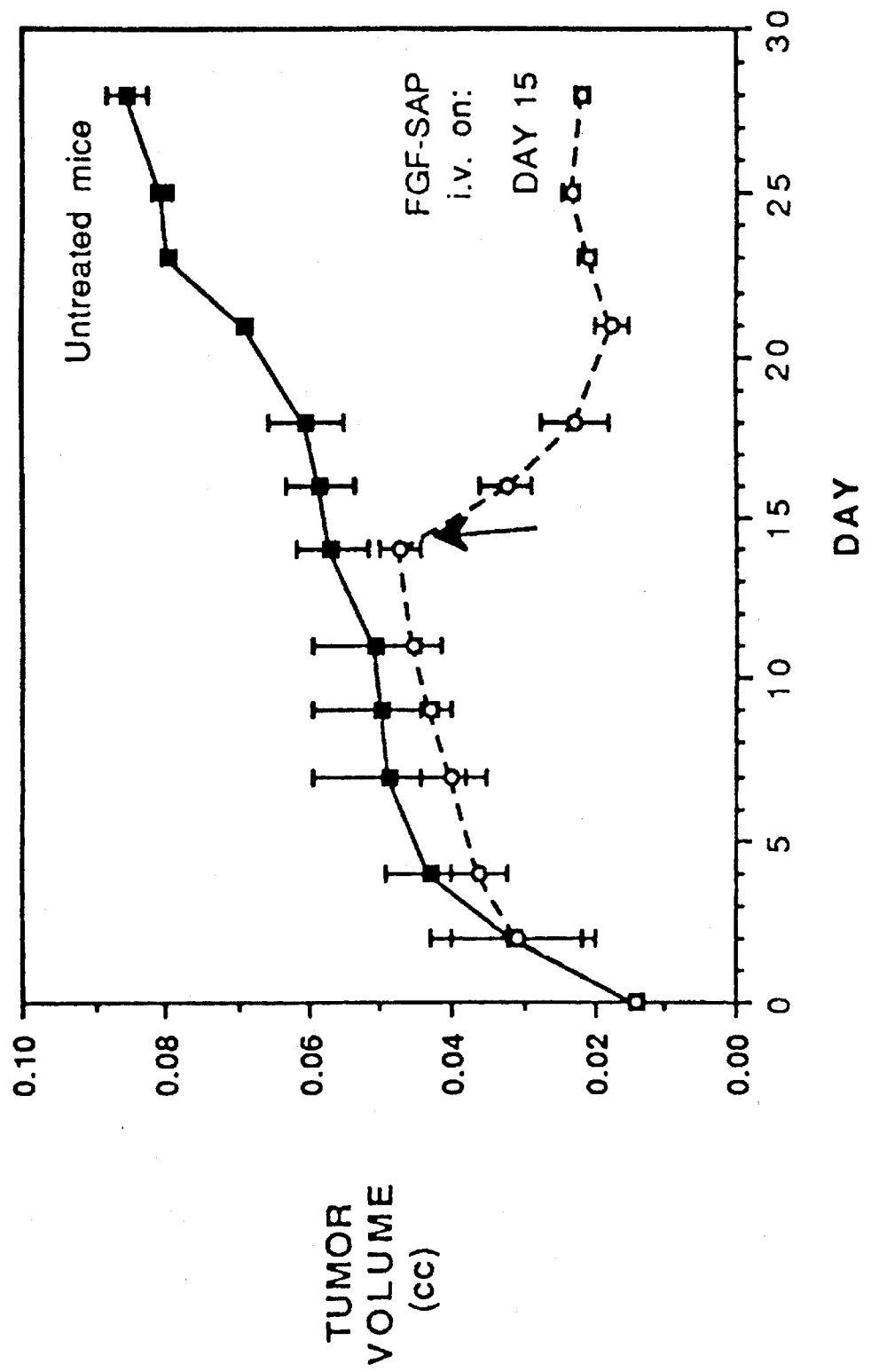

The protocol was subsequently repeated so that, as a result of the two independent studies, 10 mice were treated with respect to each individual regimen. The results of the protocol are depicted in FIGS. 1 through 5 and show that bFGF-SAP caused dramatic reductions in tumor volume within 1–2 days after administration, even when the IV treatment was delayed as much as 15 days after the initial tumor inoculation. A further study of the mice was undertaken and tabulated with respect to the condition of each mouse on day 42 of the study. It showed that all of the mice receiving the conjugate mixed with the tumor inoculum on day 0 showed complete regression of the tumors; however, in some of the IV-treated mice, complete regression of the tumors for some time period was followed by regrowth.

EXAMPLE X

SUBCUTANEOUS INJECTION OF NUDE MICE WITH FGF-SAP

The following protocol was carried out so as to compare the effect upon tumors of the Mel Tang cell line as a result of the injection subcutaneously into the lesion in nude mice.

TABLE 6

| NUMBER OF MICE | TUMOR CELL INJECTION ($2 \times 10^6$ cells) | DRUG INJECTION* |
|---|---|---|
| 5 | SQ, Day 0 | FGF-SAP SQ, Day 10 |
| 5 | SQ, Day 0 | SAP SQ, Day 10 |
|   | Autopsy   | Day 90 |

*FGF-SAP dose 0.125 mg/kg and SAP dose 0.084 mg/kg representing equivalent SAP doses The results from this protocol show that injection of the conjugate at the site of the tumor is superior to the injection of an equivalent dose of the cytotoxin saporin by itself, i.e., the conjugate-treated tumors remain small whereas the SAP-treated tumors regrow.

For treatment of a condition of interest, a therapeutically effective tumoricidal amount of a medicament containing an FGF-cytotoxic agent conjugate in a physiologically acceptable excipient is administered to a mammal. Examples of physiologically acceptable excipient include PBS and saline. Generally, the conjugate can be administered intravenously (IV) or by subcutaneous injection (SQ). The conjugate may also be administered intralesionally, where the conjugate is administered subcutaneously into the tumor site itself, or intracompartmentally, where the conjugate is injected into the peritoneal cavity. Administration of the conjugate was well tolerated by the test animal regardless of the route of administration. Overall, medicaments containing the conjugate may be particularly useful for treating patients afflicted with certain carcinomas wherein the tumor cells express FGF receptors. Some types of tumor cells may also require FGF as an autocrine growth factor, and these are believed to be particular targets against which these conjugates may be advantageously used.

The efficiency with which a cytotoxin, such as saporin or a Ricin A chain or a similar protein, can inhibit protein synthesis and consequently interfere with DNA synthesis is fairly widely known. Accordingly, the dosage of the conjugate that is administered will, to some extent, depend upon the particular cytotoxin chosen; however, doses of the conjugate in the range of about 0.01 mg to about 100 mg of the conjugate per kilogram of body weight are expected to be employed as daily dosage for treating such tumorigenic afflictions.

The toxicity of the FGF-conjugates such as FGF-SAP would be expected to vary with the cytotoxin used in the conjugate. Lower dosages of FGF-SAP were well-tolerated by most of the test animals in the Examples described above, leading to the conclusion that effective and non-toxic dosages of the conjugates may be established for human patients as well as test animals. Substantial evidence exists that FGF-conjugates, in particular, FGF-SAP, has minimal toxicity for normal tissues. Lindner et al., *Circ. Res.*, 68:106–113 (1991) found that there is little cytotoxicity of FGF-SAP for normal tissues. It is now believed that, under normal conditions, the basic FGF receptor is not expressed at high enough levels to mediate the internalization effects of the conjugate. This is compatible with the results of Whalen et al., *Growth Factors*, 1:157–164 (1989) that the systemic administration of basic FGF has little or no toxic effect. Accordingly, and surprisingly, the selective expression of FGF receptors in tumors and other pathophysiological conditions, make them exquisitely susceptible to FGF-Conjugate action.

EXAMPLE XI

FGF-CONJUGATE TOXICITY IN NUDE MICE.

Treatment with FGF-SAP or SAP was well-tolerated in the majority of animals in these studies. Subcutaneous hemorrhage and edema, accompanied by weight loss and ultimately death occurred between 10 and 14 days with the highest dose of FGF-SAP (125 μg/kg) in 10% of mice bearing SK-Mel-1, PA-1, SK-N-MC, or FSaIIC xenografts. Premature death also occurred in nearly 60% of mice bearing A431 xenografts receiving this highest FGF-SAP dose in spite of the fact that autopsies failed to reveal any gross abnormalities in vital organs and no animals died of metastatic disease. In contrast, lower doses of FGF-SAP (see Tables 3 & 4) were well-tolerated and were associated with no deaths. Furthermore, no cumulative toxicities were noted in mice receiving the multiple low-dose regimen of FGF-SAP (see Table 4). Thus, chronic treatment of tumors in vivo with low doses of FGF-SAP appeared to be both efficacious and non-toxic. No toxic side effects or premature deaths were observed either in mice receiving free SAP in the doses used or in untreated control mice.

Although the invention has been described with reference to the presently-preferred embodiments, it should be understood that various changes and modifications can be made without departing from the scope of the invention, which is defined only by the claims appended hereto.

Particular features of the invention are set forth in the claims that follow.

What is claimed is:

1. A method of treating a mammal having a tumorigenic pathophysiological condition selected from the group consisting of ovarian carcinomas, teratocarcinomas and neuroblastomas, comprising:

adminstering a therapeutically effective tumoricidal dosage of a cytotoxic conjugate, wherein:

the cytotoxic conjugate is comprised of a targeting polypeptide coupled to a cytotoxin;

the targeting polypeptide consists essentially of an FGF polypeptide that reacts with an FGF receptor;

the tumorigenic condition is one in which tumor cells or tissues are present; and the tumor cells or tissues express the FGF receptor.

2. The method of claim 1, wherein the targeting polypeptide is basic FGF.

3. The method of claim 2 wherein said cytotoxin is a ribosome-inactivating protein.

4. The method of claim 3 wherein said cytotoxin is saporin.

5. The method of claim 4 wherein said mammal is a human.

6. The method of claim 5 wherein said pathophysiological condition is an ovarian carcinoma.

7. The method of claim 5 wherein said pathophysiological condition is a teratocarcinoma.

8. The method of claim 5 wherein said pathophysiological condition is a neuroblastoma.

9. The method of claim 1, wherein the cytotoxic conjugate is administered subcutaneously.

10. The method of claim 1, wherein the cytotoxic conjugate is administered intravenously.

11. The method of claim 1, wherein the cytotoxic conjugate is administered intralesionally.

12. The method of claim 1, wherein the cytotoxic conjugate is administered intracompartmentally.

13. The method of claim 2, wherein the pathophysiological condition is an ovarian carcinoma.

14. The method of claim 2, wherein the pathophysiological condition is a teratocarcinoma.

15. The method of claim 2, wherein the pathophysiological condition is a neuroblastoma.

16. The method of claim 1, wherein the targeting polypeptide is acidic FGF.

17. The method of claim 16, wherein the pathophysiological condition is an ovarian carcinoma.

18. The method of claim 16, wherein the pathophysiological condition is a teratocarcinoma.

19. The method of claim 16, wherein the pathophysiological condition is a neuroblastoma.

* * * * *

UNITED STATES PATENT AND TRADEMARK OFFICE
CERTIFICATE OF CORRECTION

PATENT NO. : 5,478,804
DATED : December 26, 1995
INVENTOR(S) : CALABRESI, et al.

It is certified that error appears in the above-identified patent and that said Letters Patent is hereby corrected as shown below:

Title page:   Change [63] to read as follows: --
Continuation of Ser. No. 30,218    March 23, 1993, abandoned, which is national stage of PCT/US91/06680, Sept. 13, 1991, which was a continuation-in-part of U.S. Ser. No. 585,319.    Sept. 19, 1990, abandoned.--.
Column 1, change the sentence which appears at lines 8-13, to read as follows:   --This application is a continuation of U.S. application Serial No. 08/030,218 filed March 23, 1993, now abandoned, which was the national stage of PCT/US91/06680, filed September 13, 1991, which was a continuation-in-part of U.S. application Serial No. 07/585,319, filed September 19, 1990, which was abandoned.--

Signed and Sealed this

Twenty-seventh Day of August, 1996

*Attest:*

*Attesting Officer*

BRUCE LEHMAN

*Commissioner of Patents and Trademarks*